(12) United States Patent
Housen et al.

(10) Patent No.: US 9,618,433 B2
(45) Date of Patent: Apr. 11, 2017

(54) METHOD FOR CONTROLLING TENSILE STRESS DURING EVALUATION OF A BOND BETWEEN STRUCTURES

(71) Applicant: The Boeing Company, Seal Beach, CA (US)

(72) Inventors: Kevin R. Housen, Tacoma, WA (US); William J. Sweet, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 36 days.

(21) Appl. No.: 14/297,048

(22) Filed: Jun. 5, 2014

(65) Prior Publication Data
US 2015/0355062 A1    Dec. 10, 2015

(51) Int. Cl.
| | | |
|---|---|---|
| *G01N 3/10* | (2006.01) | |
| *G01N 3/24* | (2006.01) | |
| *G01N 29/04* | (2006.01) | |
| *G01N 3/08* | (2006.01) | |
| *G01M 7/08* | (2006.01) | |
| *G01N 29/00* | (2006.01) | |
| *G01N 19/04* | (2006.01) | |
| *G01N 29/11* | (2006.01) | |

(52) U.S. Cl.
CPC .............. *G01N 3/08* (2013.01); *G01M 7/08* (2013.01); *G01N 19/04* (2013.01); *G01N 29/00* (2013.01); *G01N 29/11* (2013.01); *G01N 2291/0231* (2013.01); *G01N 2291/02827* (2013.01); *G01N 2291/267* (2013.01)

(58) Field of Classification Search
CPC .............. G01N 3/00; G01N 2203/005; G01N 2203/001; G01N 3/317; G01N 2203/0016; G01N 29/2418; G01N 2291/0426; G01N 2291/0251; G01N 29/14; G01N 2291/0237; G01N 25/18; G01N 2203/0222; C21D 10/005; B23K 31/12
USPC ............. 73/827, 655, 657, 597, 602, 150 A; 356/432, 502
See application file for complete search history.

(56) References Cited

U.S. PATENT DOCUMENTS

| | | | |
|---|---|---|---|
| 7,509,876 B1 * | 3/2009 | Sokol ..................... | G01N 19/04 73/150 A |
| 2007/0039395 A1 * | 2/2007 | Gupta ..................... | C03C 17/34 73/800 |
| 2012/0100318 A1 * | 4/2012 | Danzl ................... | H01L 21/187 428/34.1 |

* cited by examiner

*Primary Examiner* — Harshad R Patel
*Assistant Examiner* — Brandi Hopkins
(74) *Attorney, Agent, or Firm* — The Boeing Company; Francisco A. Rubio-Campos

(57) ABSTRACT

A system and methods are provided for evaluating a bond between structures. The system includes an assembly of at least two bonded structures. The assembly has a front surface, a back surface, a thickness, and a bond disposed between the front surface and the back surface. At least one delay component is attached to the front surface of the assembly having a body having a front face, a back face, and a thickness. The system further includes a laser source capable of depositing laser energy onto a front face of the delay component, where a first portion of the laser energy is absorbed by the front face of the delay component to generate a first compression wave that propagates through the body of the delay component. A second portion of the laser energy is absorbed by the back face of the component to generate a second compression wave that reflects off of the back surface of the assembly to produce a tensile wave that stresses the bond.

20 Claims, 6 Drawing Sheets

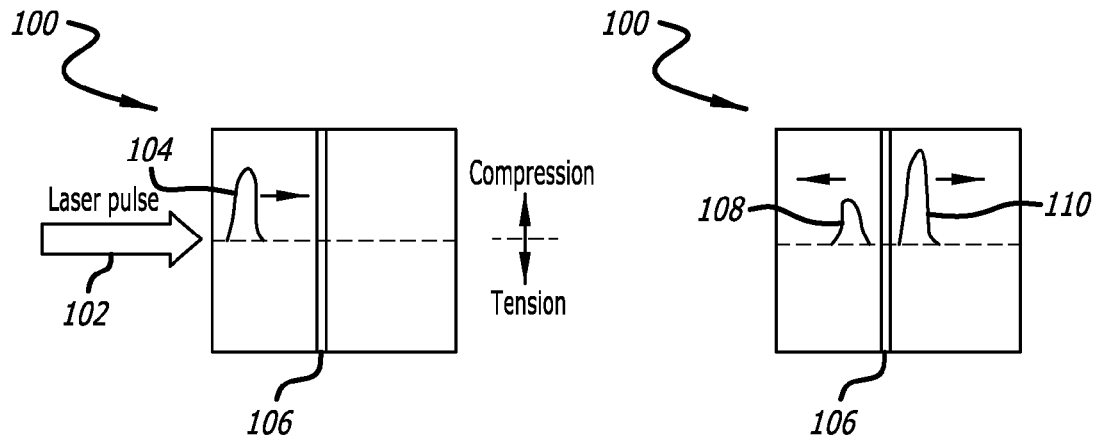
FIG. 1A
(Prior Art)
FIG. 1B
(Prior Art)
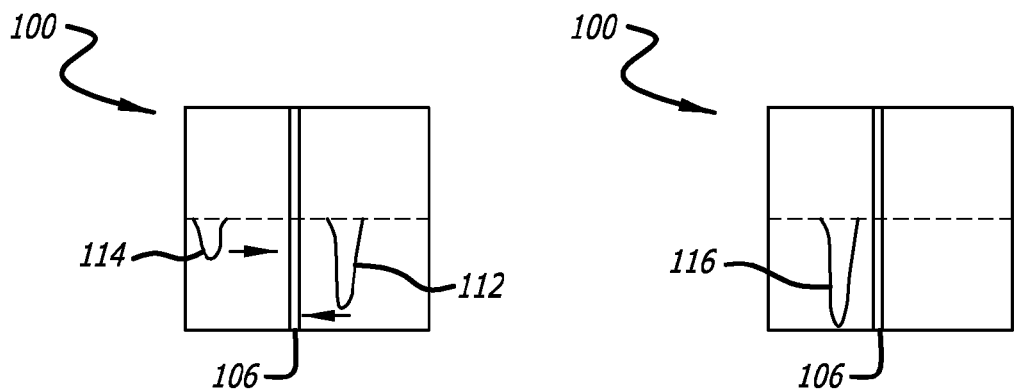
FIG. 1C
(Prior Art)
FIG. 1D
(Prior Art)

METHOD FOR CONTROLLING TENSILE STRESS DURING EVALUATION OF A BOND BETWEEN STRUCTURES

BACKGROUND INFORMATION

1. Field

The present disclosure generally relates to a system and method for evaluating bonds between structures, and, more particularly, to a system and methods for reducing tensile stresses generated during non-destructive evaluation of bonded structures.

2. Background

Bonds are widely used in a variety of structural applications, and more specifically, primary composite structures are often bonded together in select aerospace applications. Generally, the strength of the bond between composite structures must be known and certifiable if the bond is used in a primary structure application. Conventional methods for measuring bond strength generally involve static and dynamic proof testing of entire structural assemblies, subjected to simulated loads and are monitored for strain levels, which are then correlated to strength values. The structure that is tested, however, is generally a test assembly and is not used in the final assembly of the aircraft. Further, smaller component testing of individual bonds is conducted, but the components are also test assemblies and are not a part of the operational vehicle structure. Moreover, the smaller components are most frequently destructively tested.

Non-destructive inspection (NDI) methods also exist for composite structures assembled with adhesive bonds. Among other techniques, laser bond inspection (LBI) has proven useful. Laser bond inspection is a method of testing the strength of bonds between composite structures using stress waves. In this technique, weak bonds may be "pulled apart" by tension waves traveling through the structure.

With LBI, as shown in FIGS. 1(A)-1(D), a laser beam 102 is generally directed at the front surface of a bonded structure 100, which generates mechanical waves in the form of compression waves 104 that travel through the structure towards a back surface of the bonded structure 100. When the compression wave 104 reaches the back surface of the bonded structure 100, the compression wave 104 is reflected back from that surface, producing a tension wave 112 (FIG. 1c), that propagates back towards the front surface of the structure 100. The tension wave 112 applies tension to the internal makeup of the bonded structure 100, including any bond 106 holding the components of the structure 100 together.

If a tension wave 112 of sufficient strength encounters a weak bond, the bond will fail, for example, by separating. A failed bond may be detected by various techniques and methods, including, for example, ultrasonics, x-rays, and acoustics, among others commonly known in the art.

As better shown in FIG. 1(B), generally, when a compression wave 104 penetrates the structure 100 and reaches the bond 106, a portion of the compression wave 104 transfers through the bond 106 to form a transmitted wave 110 that is amplified due to the differences in the material properties, namely the wave speed (i.e., the speed of sound in the material) and density, of the bonded materials. Another portion of the compression wave 104 reflects off of the bond 106, producing a reflected compression wave 108 that propagates back towards the front surface of the composite structure 100.

As shown in FIG. 1(C), transmitted wave 110 reflects off of the back surface of the composite structure 100 producing a first tension wave 112 that propagates back towards the bond line 106. Compression wave 108 reflects off of the front surface of the composite structure 100 producing a second tension wave 114 that also propagates back towards the bond 106. Typically, the tension wave 112 reaches the bond 106 first and upon encountering the bond, this tension wave 112 subjects the bond 106 to a desired tensile stress and continues to propagate toward the front surface of the composite structure 100.

The problem with current LBI methods, as shown in FIG. 1(D), is that after tension wave 112 reaches the bond 106, it is generally transmitted through the bond 106 to combine with tension wave 114, shown in FIG. 1(C), to produce an unwanted tensile stress spike 116 in a region of the composite structure 100 between the front surface and the bond 106. This stress spike 116 often results in cracking or other mechanical failures in the composite structure 100. Thus, if the bond 106 is as strong as the composite material, the laser exposure may cause the composite material to fracture before the bond 106 is broken.

Accordingly, a need therefore exists for a system and methods for reducing tensile stress generated during non-destructive inspection of bonded composite structures.

SUMMARY

A system is provided for evaluating a bond between structures. In one example, the system may include an assembly of at least two bonded structures. The assembly includes a front surface, a back surface, a thickness, and a bond disposed between the front surface and the back surface. At least one delay component may be attached to the front surface of bonded assembly. The delay component includes a body having a front face, a back face, and a thickness. The system further includes a laser source capable of depositing laser energy onto the delay component, where a first portion of the laser energy is absorbed by the front face of the delay component to generate an initial compression wave that propagates through the body of the delay component. A second portion of the laser energy is absorbed by the back face of the delay component to generate a second compression wave that reflects off of the back surface of the assembly to produce a tension wave that stresses the bond.

A method for evaluating the strength of a bond in a bonded assembly is also provided, where the bonded assembly includes a front surface and a back surface and a thickness therebetween. The method includes attaching at least one delay component to the front surface of the bonded assembly structure. The delay component may include a body having a front face, a back face, and a thickness. The method further includes positioning a laser source near the front face of the delay component, depositing laser energy onto the front face of the delay component to generate an initial compression wave that propagates through the body of the delay component, and depositing laser energy onto the back face of the delay component to generate a second compression wave that propagates through the bonded assembly and reflects off of the back surface to produce a tension wave that stresses the bond.

A first portion of the second compression wave reflects off of the bond, generating a reflected compression wave that travels from the bond back toward the front surface of the bonded assembly. The reflected compression wave combines with the initial compression wave at the front surface to produce a net compression wave that travels from the front surface, back towards the bond. A second portion of the second compression wave transmits through the bond and encounters the back surface of the bonded assembly, where it is reflected, generating a tension wave that propagates from the back surface towards the bond. Upon encountering the bond, this tension wave subjects the bond to a desired tensile stress and continues to propagate towards the front surface of the bonded assembly. At a location away from the bond, the net compression destructively interferes with the tension wave to reduce the tensile stress spiking in this region.

A method for non-destructive bond evaluation is further provided. The method includes providing a bonded assembly of at least two structures having a front surface, a back surface, and a bond disposed between the front surface and the back surface. The method further includes attaching a plurality of layered n delay components to the front surface of the bonded assembly, where each delay component comprises a body having a front face, a back face, and a thickness. Next, laser energy may be deposited onto the layered delay components to generate n+1 compression waves that cooperatively interact to produce a tension wave that penetrates the bonded assembly to stress the bond. Finally, the bond t may be inspected to determine if the integrity of the bond has been compromised. Under this method, a resulting compression wave generated by the plurality of delay components combines with a reflected compression wave generated by the n+1 compression wave to reduce tensile stresses generated in the bonded assembly.

Other devices, apparatus, systems, methods, features and advantages of the disclosure will be or will become apparent to one with skill in the art upon examination of the following figures and detailed description. It is intended that all such additional systems, methods, features and advantages be included within this description, and be protected by the accompanying claims.

BRIEF DESCRIPTION OF THE FIGURES

The present disclosure may be better understood by referring to the following figures. The components in the figures are not necessarily to scale, emphasis instead being placed upon illustrating the principles of the disclosure. In the figures, like reference numerals designate corresponding parts throughout the different views.

FIGS. 1(A)-1(D) (Prior Art) are schematics illustrating an existing laser bond inspection process.

DETAILED DESCRIPTION

FIGS. 2-8 illustrate examples of systems and methods for reducing tensile stresses generated during non-destructive evaluation of a bonded assembly consisting of two or more materials. One or both materials may be a composite or metallic material. The disclosed systems and methods are useful in any field in which non-destructive bond evaluation is required or desired.

Figure 2:
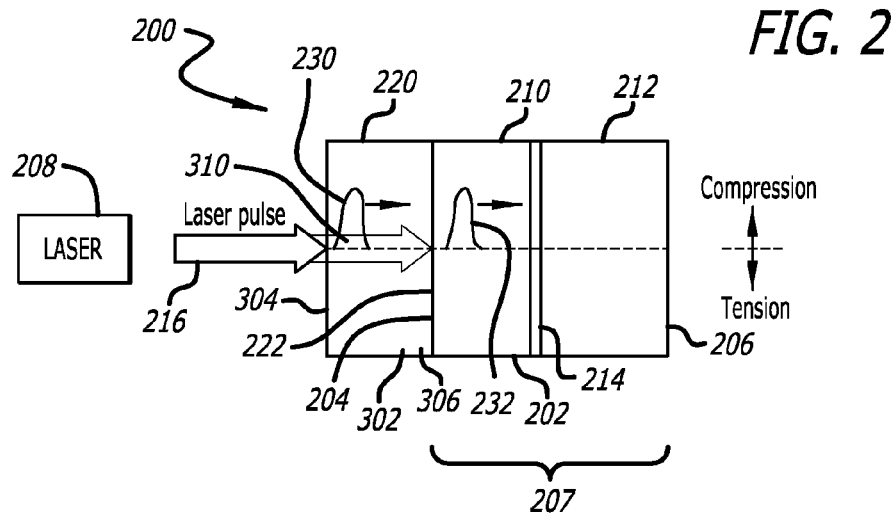
FIG. 2 is a schematic illustrating one example of a non-destructive bond evaluation system of the present disclosure at a first point in time.

FIG. 2 is a schematic illustrating one example of a system 200 for evaluating the strength of a bond between composite structures in accordance with the present invention. The system 200 may include a bonded assembly 202 consisting of a first composite structure 210 adhesively bonded to a second composite structure 212. The assembly 202 further includes a front surface 204, back surface 206 and thickness 207, and a laser source 208 oriented toward the front surface 204 of the bonded assembly 202. One of ordinary skill in the art will readily recognize that the proximity and/or orientation of the laser source 208 relative to the bonded assembly 202 may vary, and may be any operable or workable range and/or displacement appropriate for the strength of the laser.

The first composite structure 210 of the bonded assembly 202 may be bonded by an adhesive via bond 214 to the second composite structure 212. The adhesive may be comprised of, for example, film or paste epoxy. The first composite structure 210 and the second composite structure 212 may be made of any type of material, including, but not limited to, composites and metallic materials provided that the acoustic impedance of the first composite structure 210 is lower than the acoustic impedance of the second composite structure 212.

In most applications, is it is preferred that the first composite structure 210 and second composite structure 212 are made of dissimilar materials, as composite structures made of the same material do not reflect waves as taught by the present invention, but only transmit waves across the boundary of the two materials. As used herein, dissimilar means the materials have different densities and/or different acoustic impedances. For example, in one implementation, the first composite structure 210 may include a composite material and the second composite structure 212 may include a metal. In other implementations, the first and second structures 210, 212 may include any combination of composites, metals, plastics, or other bondable materials, provided that the acoustic impedance of the first composite structure 210 is lower than the acoustic impedance of the second composite structure 212.

It should be noted that the ease with which a pressure or stress wave travels through a material depends on a property of the material called acoustic impedance (Z). The acoustic impedance of a material is defined as the product of the density of the material and its acoustic wave speed (i.e., the speed that sound travels through the material). Acoustic impedance is important in determining the acoustic transmission and reflection at the boundary of two materials having different acoustic impedances. The ratio of the reflected wave intensity $I_r$ to the incident wave intensity ($I_o$) is given by:

$$I_r/I_o = (Z_2-Z_1)^2/(Z_2+Z_1)^2$$

Thus, the greater the difference between the acoustic impedances of two materials at a boundary in a composite structure, the greater the amount of reflection. For example, two materials with the same acoustic impedance would give no reflection (or refraction), while two materials with widely separated values would generate much larger reflections.

With respect to the present disclosure, when a pressure wave encounters a difference in the acoustic impedance of a material, the pressure wave reflects in a way that depends on whether the pressure wave is moving from a material with high impedance to a material with low impedance, or a material with low impedance to a material with high impedance. For instance, when a pressure wave travels from a material that has a high acoustic impedance to one that has a low impedance, the pressure wave will reflect at the interface and change either from compression to tension, or from tension to compression. In the alternative, a pressure wave reflects in compression when a pressure wave is travels from a material that has a low acoustic impedance to one that has a higher impedance.

The laser beam source 208 may be any source known the in the art. The laser beam source 208 may be adapted to generate a laser pulse 216 having laser energy that penetrates the bonded assembly 202, resulting in the generation of an alternating sequence of compression and tension waves that combine to produce tensile stresses in the bonded assembly 202. The tensile stresses are used to test the strength of the bond 214. In some implementations, the laser beam source 208 may comprise a single-shot, high peak power laser with short pulse duration (e.g., 100 nanoseconds). In other implementations, the laser beam source 208 may generate an annular laser beam and/or may also be a part of a laser shock processing assembly. Such assemblies and methods are described, for example, in U.S. Pat. Nos. 5,741,559, 5,911,891, 6,412,331, 5,131,957, 7,735,337, and U.S. application Ser. No. 10/950,865, each of which is incorporated by reference herein in its entirety. Also, in assemblies, such as annular laser beam assemblies and methods described in U.S. Pat. No. 7,735,377, a specific depth of inspection may be selected by adjusting the ratio of the inner diameter relative to the outer diameter of the annular laser beam.

As shown in FIG. 2, a delay component 220 may be attached to the front surface 204 of the first composite structure 210 of bonded assembly 202 along an interface 222, such that the delay component 220 is disposed between the laser source 208 and the bonded assembly 202. The delay component 220 may be attached to the front surface 204 of the bonded assembly 202 by an adhesive or other suitable means.

The function of the delay component 220 is to create a time delay between the arrival of compression waves generated by the laser pulse 216 at a front face and back face of the delay component 220, as described in detail below. As used herein, the term "delay" generally refers to the time it takes a compression wave to travel from a front face of the delay component 220 to a back face of the component.

Figure 3:
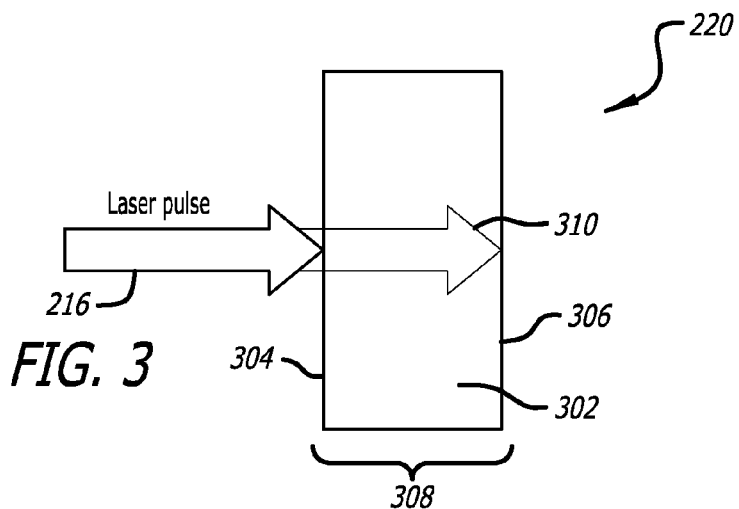
FIG. 3 is a schematic illustrating an example delay component according to one example of the present disclosure.

As better shown in FIG. 3, the delay component 220 may include a body 302 having a front face 304, a back face 306, and a thickness 308. The thickness 308 of the delay component 220 may vary based on the time delay desired by the user.

The delay component 220 may be made of material that is transparent to laser light. For purposes of the present disclosure, transparent material refers to any material that allows light to pass through the material without being attenuated. For example, such transparent material may include acrylic or polycarbonate. Other examples of materials with substantially transparent properties include sapphire and quartz, which may be used if a high sound wave speed is desired for purposes of timing the compression wave delay.

In certain implementations, a layer of substantially opaque material, for example, a layer of black paint applied in a grid pattern, may be adhered to the front face 304 of the delay component 220 to absorb a portion of the laser energy of the laser pulse 216. This allows the magnitude of compression waves generated at the front face 304 relative to that of the back face 306 to be controlled, as discussed in detail below. In these implementations, the layer of opaque material on the front face 304 may comprise a pattern of pixels; for example, checkered or circular pixels. In other implementations, the pattern of pixels may comprise a series of spaced lines. As such, a portion of the laser light is absorbed by each pixel, while unabsorbed portions of light are allowed to pass through the pixel pattern toward the back face 306 of the delay component 220. The magnitude of the compression waves generated at the front face 304 relative to that of the back face 306 may be controlled, for example, by adjusting the density of the pixel pattern. The back face 306 in this example may be coated with a solid layer or material, for example, a solid layer of paint, to absorb the remaining portion of laser light.

FIG. 2, in conjunction with FIGS. 3-6, illustrates how compression and tensile waves are generated in the system 200. When laser pulse 216 is applied to the bonded assembly 202, the front face 304 of the delay component 220 is struck first by laser pulse 216. The laser energy absorbed at the front face 304 of the delay component 220 generates an initial compression wave 230 that propagates through the body 302. Because the delay component 220 is transparent to the laser light, the transmitted portion 310 of laser light 216 penetrates the body 302 to strike the back face 306 of the delay component 220, where the laser energy of the transmitted portion 310 is absorbed, to generate a second compression wave 232 that propagates through the first composite structure 210 of the bonded assembly 202, towards the bond 214.

Depending on the material properties of the delay component 220 relative to the material properties of the first composite structure 210, the amplitude of the initial compression wave 230 may be equal to or greater than the amplitude of the second compression wave 232 (FIG. 2). Further, if the user desires the initial compression wave 230 to have a higher amplitude than the second compression wave 232, the user may alter the grid pattern of the opaque material adhered to the front face 304 of the delay component 220 to enable more laser energy to be deposited (i.e., absorbed) at the front face 304 of the delay component 220.

Figure 4:
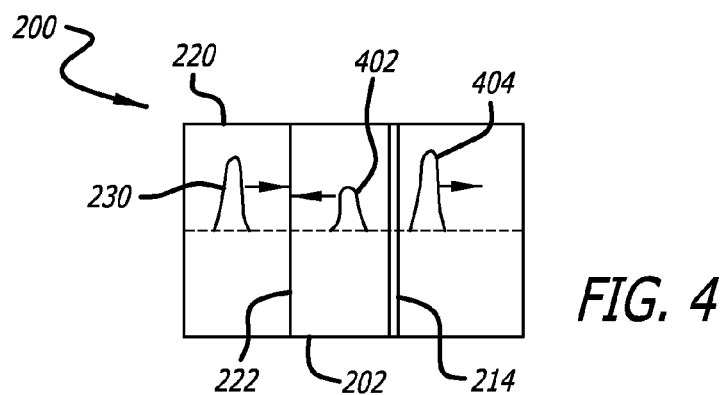
FIG. 4 is a schematic illustration of the system of FIG. 2 at a second point in time.

FIG. 4 is a schematic illustration of system 200 at a second point in time. As shown, once the second compression wave 232 reaches the bond 214, because the acoustic impedance of the first composite structure 210 is lower than that of the second composite structure 212, a portion of the second compression wave 232 reflects off of the bond 214, producing a reflected compression wave 402 that propagates back towards the front surface 204 of the bonded assembly 202. Reflected wave 402 is that part of the second compression wave 232 that reflects back from the bond joint 214 due to the dissimilar material properties of the first composite structure 210 and the second composite structure 212, as further explained above. When traveling from the bond joint 214 to the front surface 204 of the bonded assembly 202, the reflected wave 402 causes compression in the first composite structure 210.

While a first portion of the second compression wave 232 reflects off of the bond joint 214 forming reflected compression wave 402, a second portion of the second compression wave 232 is transferred through the bond joint 214 to generate a transmitted compression wave 404 that travels from the bond 214 to the back surface 206 of the bonded assembly 202. When traveling from the bond 214 to the back surface 206 of the assembly 202, transmitted wave 404 causes compression in the second composite structure 212. Transmitted wave 404 may, for example, get amplified over the amplitude of the reflected compression wave 402 due to the difference in the wave speed and the material properties of the second composite structure 212 from the first composite structure 210 of the bonded assembly 202.

Figure 5:
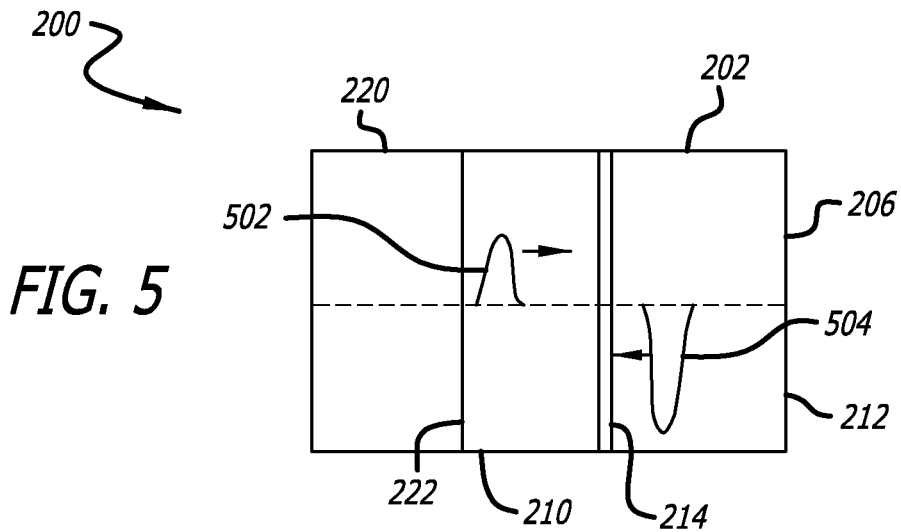
FIG. 5 is a schematic illustration of the system of FIG. 2 at a third point in time.

FIG. 5 is a schematic illustration of system 200 at a third point in time. At this instance, the initial compression wave 230 (FIGS. 2 & 4) arrives at interface 222 at approximately the same time as reflected compression wave 402 (FIG. 4). The initial compression wave 230 destructively interferes with compression wave 402 to produce a net compression wave 502. Because the amplitude of the initial compression wave 230 is generally greater than the amplitude of compression wave 402, the interference of the pressure waves typically produces a net compression wave 502 that propagates back towards the bond 214.

FIG. 5 further illustrates that, around this point in time, transmitted wave 404 (FIG. 4) reflects off of the back surface 206 of the bonded assembly 202, generating a tension wave 504 that propagates towards the bond joint 214. When traveling from the back surface 206 of the bonded assembly 202 to the bond 214, tension wave 504 causes tension in the second composite structure 212. Because air has a lower acoustic impedance that the second composite structure 212, approximately 100% of transmitted wave 404 is reflected and converted from a compression wave to a tension wave 504.

Figure 6:
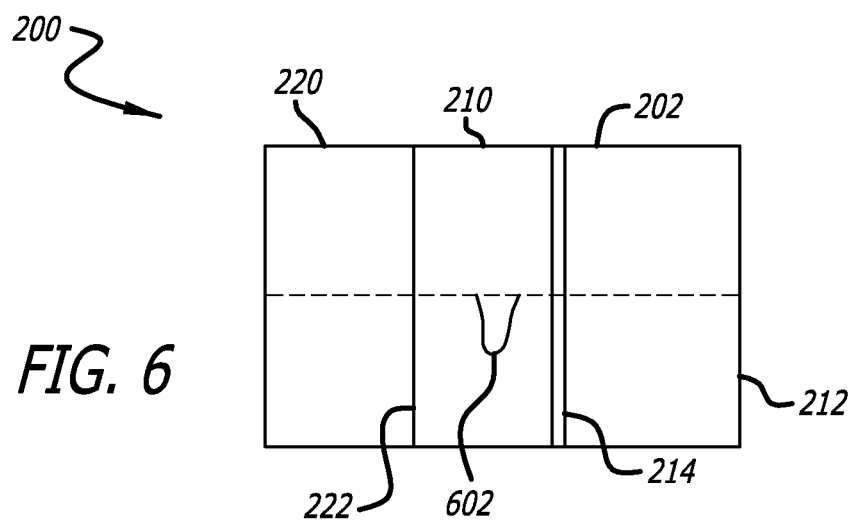
FIG. 6 is a schematic illustration of the system of FIG. 2 at a fourth point in time.

FIG. 6 is a schematic illustration of system 200 at a fourth point in time. At this instance, tension wave 504 (FIG. 5) has reached the bond 214 to subject the bond to tension stress. After tension wave 504 reaches the bond 214, tension wave 504 is transmitted through the bond 214 into the first composite structure 210 and combines with compression wave 502 (FIG. 5) to reduce a peak in tensile stress 602 typically applied to the first composite structure 210. The abated tensile stress 602 minimizes the probability of cracking or other mechanical failures typically experienced by bonded structures during laser inspection.

Once the bond 214 has been stressed, the bond 214 may then be examined to see if there is any separation or dissociation of the bond 214. If the bond 214 has not been broken, this indicates to the user that the integrity of the bond 214 has been maintained. The integrity of the bond 214 may be examined by any conventional method or and technique known in the art, such as, for example, ultrasound after laser exposure, a Velocity Interferometer System for Any Reflector (VISAR), an electromagnetic acoustic transducer, capacitance probes, or piezoelectric ultrasonic transducers.

The delay component 220 creates a time delay between the first and second compression waves 230 and 232 that can be altered to affect the timing of the interactions between the alternating compression and tension waves. The time delay may be controlled by either altering the thickness 308 of the delay component 222, or altering the acoustic wave speed of the delay component 222 by changing its material. In this way, a single laser pulse 216 can be used to generate a pair of compression waves 230, 232 in the bonded assembly 202, separated by a desired time interval. With respect to altering the thickness of the delay component 220 material, the thickness of the delay component 220 will determine how long it will take the initial compression wave 230 to reach the interface 222.

Figure 7:
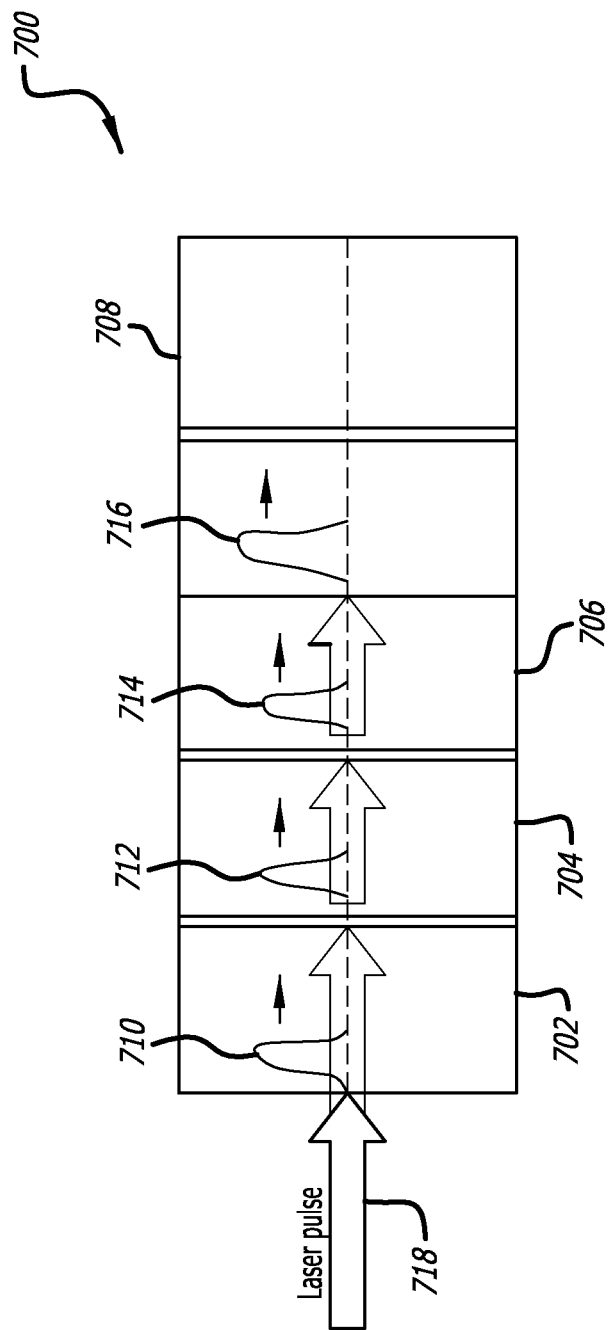
FIG. 7 is a schematic illustrating another example of a non-destructive bond evaluation system according the present disclosure.

FIG. 7 is a schematic illustrating another example of a bond evaluation system 700 of the present disclosure. In this example, the system 700 incorporates a plurality of delay components 702, 704, 706 stacked together upstream of the bonded assembly 708. In this way, multiple compression waves 710, 712, 714 and 716 may be generated from a single laser pulse 718 by layering the delay components 702, 704, 706. A principal reason for using a plurality of delay components is to sequence the arrival of the multiple compression waves 710, 712, 714 in an advantageous way to reduce the magnitude of the tensile stress 602 (FIG. 6) in the bonded assembly 708. The arrival time of the compression wave from each delay component can be controlled by adjusting the thickness or the wave speed of each delay component. For example, the arrival times could be adjusted so that the plurality of compression waves 710, 712, 714 arrive one right after the other, thereby creating essentially a net compression wave which may be used to reduce or eliminate the peak in tensile stress 602 (FIG. 6) formed in the bonded assembly 708.

In this example, the front and back faces of the first two delay components 702, 704 downstream of the laser (not shown), and the front face of the last delay component 706 may comprise pixel patterns that permit unabsorbed portions of laser light to pass through the delay components 702, 704, 706 towards the back face of delay component 706. The back face of delay component 706 may comprise a solid layer of material, for example, a solid layer of black paint, to absorb the remaining laser energy.

Figure 8:
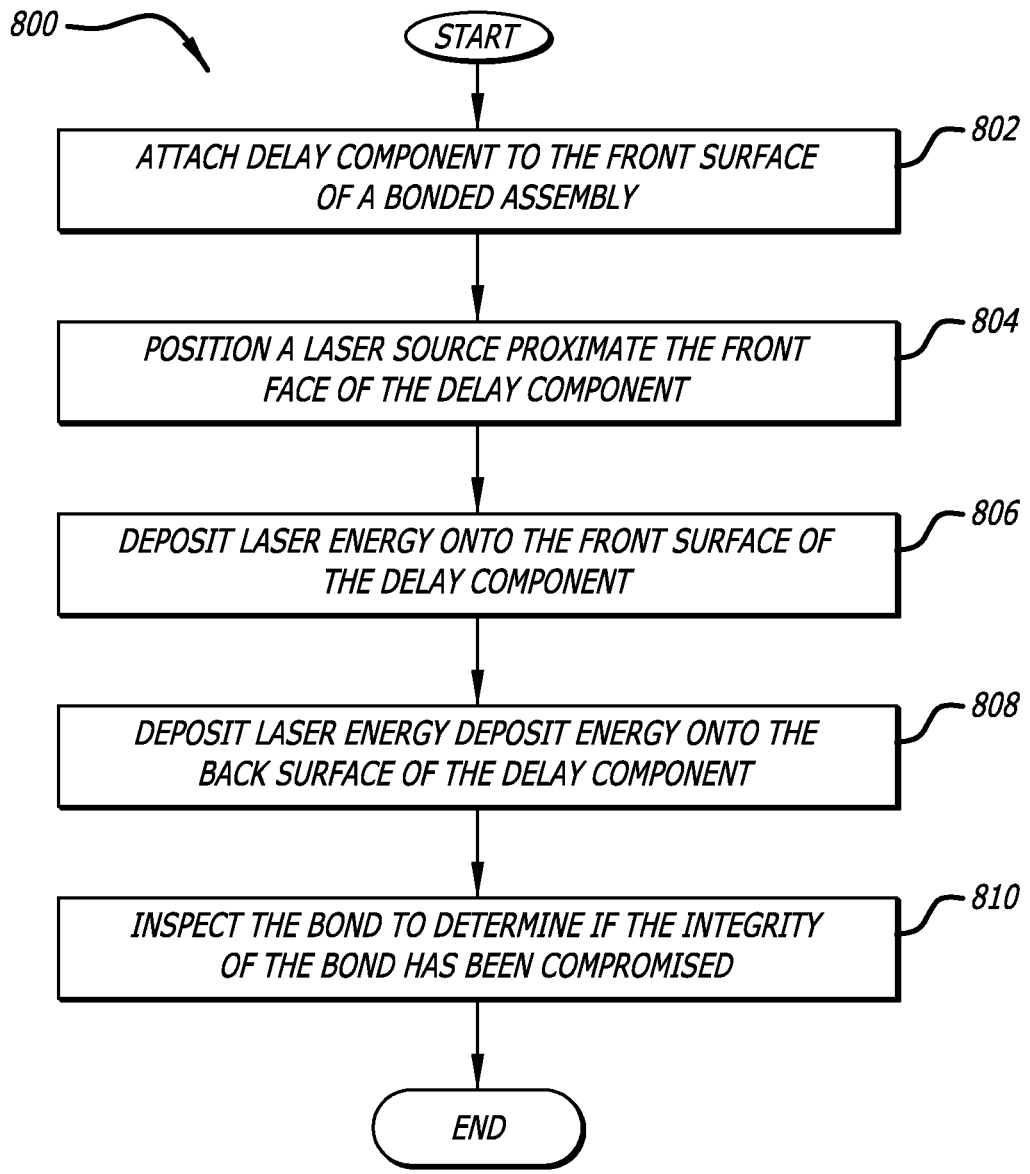
FIG. 8 illustrates a flow diagram of one example of a process for reducing tensile stresses generated during non-destructive inspection of a bonded assembly according to the present disclosure.

With reference now to FIG. 8, a process for evaluating the bond strength of a bonded assembly is illustrated in flow diagram 800. The process begins by attaching a delay component to a front surface of the bonded assembly (step 802). As described above, the delay component may include a body having a front face, a back face, and a thickness. Next, a laser source is positioned proximate the front face of the delay component (step 804). A laser beam of coherent light is then directed at the front surface of the delay component, depositing laser energy onto the front face and back face of the delay component (steps 806, 808). In these steps, the laser energy deposited on the front face of the delay component produces an initial compression wave that propagates through the body of the delay component. The laser energy deposited onto the back face of the delay component produces a second compression wave that propagates through the bonded assembly towards the bond. A first portion of the second compression wave reflects off of the bond, generating a reflected compression wave that travels from the bond joint back towards the front surface of the bonded assembly. The reflected compression wave combines with the initial compression wave at the front surface of the bonded assembly to produce a, third, net compression wave that travels back through the bonded assembly, from the front surface towards the bond.

Further, during step 808, a second portion of the second compression wave is transmitted through the bond and reflects off of the back surface of the bonded assembly, generating a tension wave that travels from the back surface back towards the bond. The net compression wave traveling from the front surface of the bonded assembly destructively interferes with the tension wave at a location away from the bond to reduce the peak tensile stress ordinarily experienced in the bonded assembly after the tension wave transmits through the bond.

In a final step, the bond joint is inspected to determine if the integrity of the bond has been compromised (step 810). For example, in certain inspection methods a low-intensity test signal or laser pulse may be sent through the bonded assembly before and after the bond is stressed and the responses caused by the test signals are compared to determine if the bond has been compromised. In other methods, for example, a low-intensity test signal or laser pulse may be sent through the bonded assembly before and after the bond is stressed, where the frequency of vibration of a surface of the bonded assembly caused by the test signals may be compared to determine if the bond has been compromised.

Figure 9:
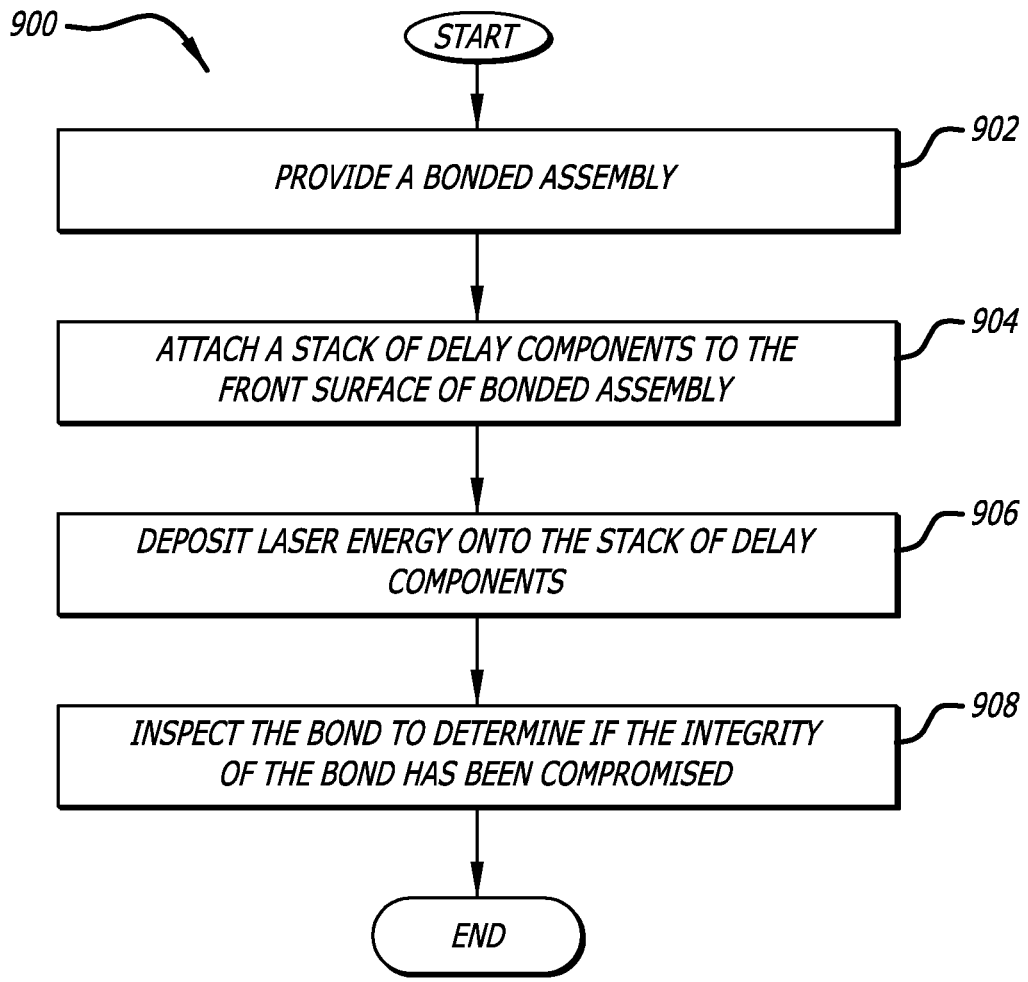
FIG. 9 illustrates a flow diagram of another example of a process for reducing tensile stresses generated during non-destructive inspection of a bonded assembly according to the present disclosure.

FIG. 9 illustrates a flow diagram 900 of another process of reducing tensile stresses generated during non-destructive evaluation of a bonded assembly. According to this implementation, the process starts by providing a bonded assembly comprised of at least two structures (step 902). The bonded assembly may include a front surface, a back surface, and a bond disposed between the front surface and the back surface. Next, a sub-assembly comprising a stack of n delay components (where n is a positive integer greater than or equal to 1) is attached the front surface of the composite structure (step 904). Each component includes a body made of transparent material. The body includes a front face, a back face, and a thickness.

At step 906, a laser beam of coherent light is directed at the front surface of the stack of delay components, depositing laser energy onto the sub-assembly to generate an n+1 compression wave that cooperatively interacts to both produce a tension wave that penetrates the bonded assembly and stresses the bond, and reduce peak tensile stresses generated in the composite structure that cause the structure to crack.

After the bond has been stressed, the bond is inspected to determine if the integrity of the bond has been compromised (step 908).

In general, terms such as "attached to," "coupled to," and "configured for coupling to" and "secured to" (for example, a first component is "coupled to" or "is configured for coupling to" or is "secured to" a second component), or "communicate" (for example, a first component "communicates with" or "is in communication with" a second component) are used in this application to indicate a structural, functional, mechanical, electrical, signal, optical, magnetic, electromagnetic, ionic or fluidic relationship between two or more components (or elements, features, or the like). As such, the fact that one component is said to couple to a second component is not intended to exclude the possibility that additional components may be present between, and/or operatively associated or engaged with, the first and second components.

The present disclosure may be applied to any application where two materials are bonded together by an adhesive. Although the previous description illustrates particular examples of various implementations, the present disclosure is not limited to the foregoing illustrative examples. A person skilled in the art is aware that the disclosure as defined by the appended claims can be applied in various further implementations and modifications. In particular, a combination of the various features of the described implementations is possible, as far as these features are not in contradiction with each other. Accordingly, the foregoing description of implementations has been presented for purposes of illustration and description. Modifications and variations are possible in light of the above description.

What is claimed is:

1. A system for non-destructive evaluation of a bond between structures, the system comprising:
    an assembly of at least two bonded structures having different acoustic impedances, the assembly having a front surface, a back surface, and a bond to be evaluated disposed between the structures;
    at least one delay component attached to the front surface of the assembly, the delay component comprising a body having a front face, a back face, and a thickness; and
    a laser source configured to deposit at least one pulse of laser energy onto the front face of the at least one delay component, wherein a first portion of the laser energy is absorbed by the front face of the at least one delay component to generate an initial compression wave that propagates through the body of the at least one delay component, and wherein a second portion of the laser energy passes through the body of the at least one delay component and is absorbed by the back face of the at least one delay component to generate a second compression wave that reflects off of the back surface of the assembly to produce a tension wave that stresses the bond.

2. The system of claim 1, wherein the at least one delay component is substantially transparent to light.

3. The system of claim 1, wherein the at least two bonded structures comprise a first structure and a second structure wherein the acoustic impedance of the first structure is lower than the acoustic impedance of the second structure.

4. The system of claim 1, wherein a grid pattern comprising opaque material is adhered to the front face of the delay component, and wherein the magnitude of the initial compression wave relative to the second compression wave may be adjusted by adjusting the grid pattern.

5. The system of claim 1, wherein the delay component creates a time delay between the propagation of the initial compression wave through the delay component relative to the propagation of the second compression wave through the bonded assembly.

6. The system of claim 5, wherein the time delay may be altered by changing either the thickness of the delay component or the delay component material.

7. The system of claim 1, wherein a portion of the second compression wave reflects off the bond, generating a reflected compression wave that propagates from the bond line to the front surface of the bonded assembly, and wherein the reflected compression wave meets and destructively interferes with the initial compression wave at the front surface to generate a net compression wave that propagates from the front surface to the bond line.

8. The system of claim 1, wherein the net compression wave combines with the tension wave to reduce tensile stresses generated in the bonded assembly in regions away from the bond.

9. The system of claim 1, wherein a plurality of layers of two or more delay components are attached to the front surface of the bonded assembly.

10. A method for evaluating the strength of a bond in a bonded assembly having a front surface and a back surface, the method comprising:
    attaching at least one delay component to the front surface of the bonded assembly to be evaluated, the delay component comprising a body having a front face, a back face, and a thickness;

depositing at least one pulse of laser energy onto the front face of the delay component, a first portion of the laser energy generating an initial compression wave that propagates through the body of the delay component; and depositing a second portion of the laser energy onto the back face of the delay component to generate a second compression wave that propagates through the bonded assembly and reflects off of the back surface to produce a tension wave that stresses the bond.

11. The method of claim 10, wherein a first portion of the second compression wave reflects from the bond, generating a reflected compression wave that propagates from the bond towards the front surface of the bonded assembly, and wherein the reflected compression wave combines with the initial compression wave at the front surface of the bonded assembly to produce a net compression wave that propagates from the front surface towards the bond.

12. The method of claim 11, wherein
a second portion of the second compression wave is transmitted through the bond, generating a transmitted compression wave that propagates from the bond to the back surface of the bonded assembly,
wherein the transmitted compression wave reflects off of the back surface of the bonded assembly, generating a tension wave the propagates from the back surface towards the bond, and
wherein the net compression wave destructively interferes the tension wave to reduce tensile stresses generated in the bonded assembly.

13. The method of claim 10, further comprising the step of adhering a pattern of opaque material to the front face of the delay component, wherein the magnitude of the initial compression wave relative to the second compression wave may be adjusted by adjusting the pattern.

14. The method of claim 10, wherein the at least one component is substantially transparent to light.

15. The method of claim 10, wherein the bonded assembly comprises a first structure and a second structure wherein the acoustic impedance of the first structure is lower than the acoustic impedance of the second structure.

16. The method of claim 10, wherein the delay component creates a time delay between the propagation of the initial compression wave through the component relative to the propagation of the second compression wave through the bonded assembly, and wherein the time delay may be altered by changing either the thickness of the delay component or the delay component material.

17. The method of claim 10, wherein a stack of two or more delay components are attached to the front surface of the bonded assembly.

18. The method of claim 10, further comprising the step of inspecting the bond to determine if the integrity of the bond has been compromised.

19. A method for non-destructive bond evaluation, the method comprising:
providing a bonded assembly of at least two structures, the assembly having a front surface, a back surface, and a bond joint to be evaluated disposed between the front surface and the back surface;
attaching a plurality of n delay components to the front surface of the bonded assembly, wherein each delay component comprises a body having a front face, a back face, and a thickness;
depositing at least one pulse of laser energy onto the plurality of delay components to generate an n+1 compression wave that produces a tension wave that penetrates the bonded assembly to stress the bond; and
inspecting the bond to determine if the integrity of the bond has been compromised,
wherein n is a positive integer greater than or equal to 1.

20. The method of claim 19, wherein a resulting compression wave generated by the plurality of n delay components combine with a reflected compression wave generated by the n+1 compression wave to reduce tensile stresses generated in the bond assembly.

* * * * *